United States Patent [19]

Obenchain

[11] Patent Number: 5,562,695
[45] Date of Patent: Oct. 8, 1996

[54] NERVE DEFLECTING CONDUIT NEEDLE AND METHOD

[76] Inventor: Theodore G. Obenchain, 355 E. Grand Ave., Escondido, Calif. 92025-3336

[21] Appl. No.: 370,989

[22] Filed: Jan. 10, 1995

[51] Int. Cl.⁶ ..................................................... A61B 17/34
[52] U.S. Cl. .............................................. 606/185; 606/167
[58] Field of Search ........................... 606/1, 61, 96, 606/98, 167, 185, 223, 224; 604/164, 264, 272

[56] References Cited

U.S. PATENT DOCUMENTS

| | | | |
|---|---|---|---|
| 4,545,374 | 10/1985 | Jacobson . | |
| 4,573,448 | 3/1986 | Kambin | 606/170 |
| 4,581,025 | 4/1986 | Timmermans | 604/264 |
| 4,638,799 | 1/1987 | Moore | 606/1 |
| 5,112,335 | 5/1992 | Laboureau et al. | 606/88 |
| 5,195,541 | 3/1993 | Obenchain | 128/898 |
| 5,201,729 | 4/1993 | Hertzmann et al. . | |
| 5,254,106 | 10/1993 | Feaster | 604/272 |
| 5,275,611 | 1/1994 | Behl | 606/198 |
| 5,312,360 | 5/1994 | Behl | 604/164 |
| 5,313,962 | 5/1994 | Obenchain | 128/898 |
| 5,314,429 | 5/1994 | Goble | 606/96 |
| 5,437,661 | 8/1995 | Rieser . | |
| 5,449,351 | 9/1995 | Zohmann | 604/272 |

OTHER PUBLICATIONS

William A. Friedman, M.D., (1983) Percutaneous Discectomy: An Alternative to Chemonucleolysis? Neurosurgery 13(5):542–547.
"Sales Brochure" for ViewPoint™ surgical workstation. Picker International, Cleveland, Ohio.

*Primary Examiner*—Michael H. Thaler
*Assistant Examiner*—Patrick W. Rasche
*Attorney, Agent, or Firm*—Jerry R. Seiler, Esq.

[57] ABSTRACT

This invention relates to devices and methods for accessing the spinal epidural space via the neural foramen. In one aspect of this invention a deflecting conduit needle device is disclosed having an elongated body extending substantially along a first axis. The device has a proximal end and a distal end, and a transverse conduit, positioned along the distal one-eighth of the device and extending substantially along a second axis, wherein the second axis is positioned at an acute angle relative to the first axis. In another aspect of the invention a method is disclosed for accessing the spinal epidural space via the neural foramen.

33 Claims, 7 Drawing Sheets

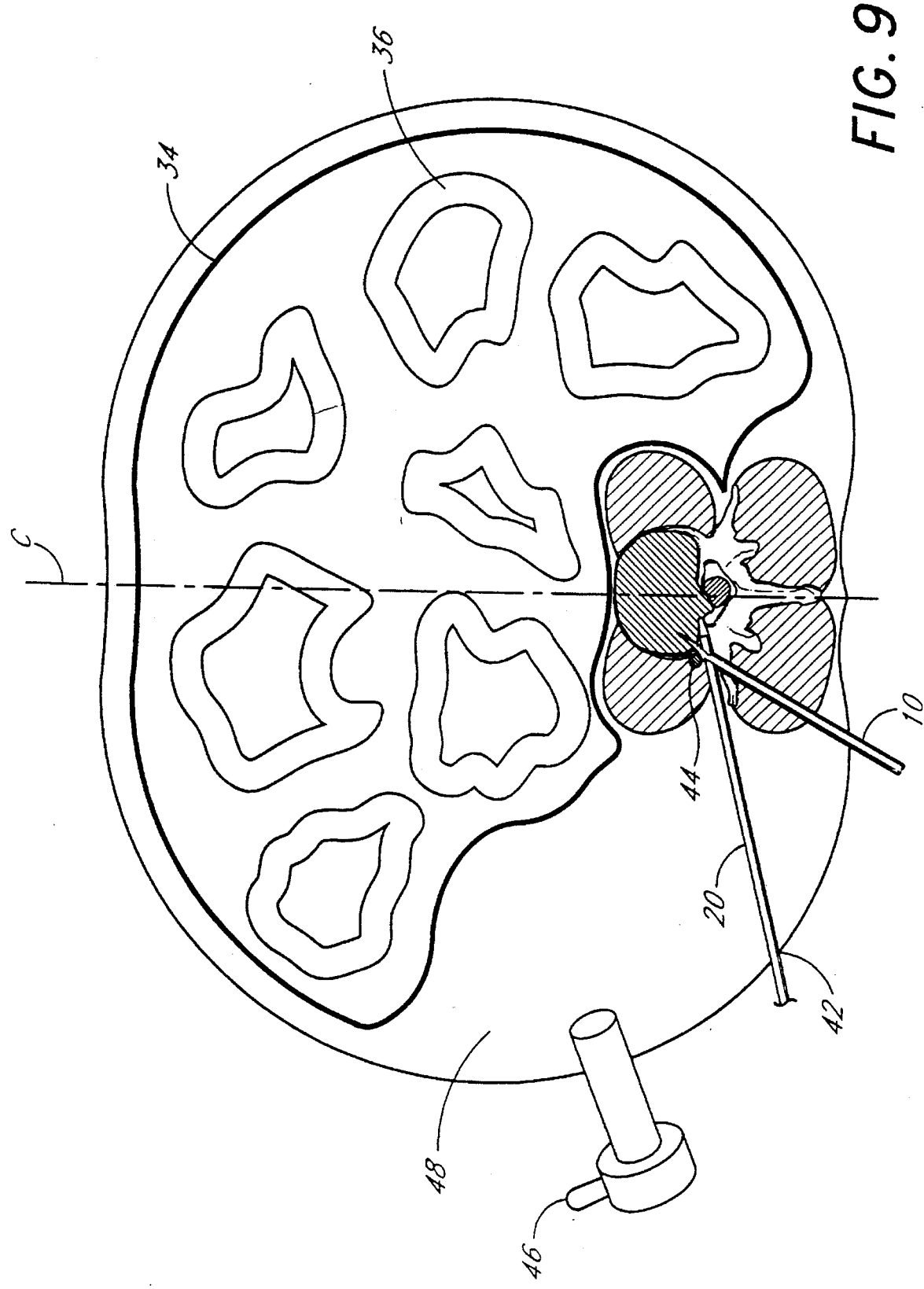

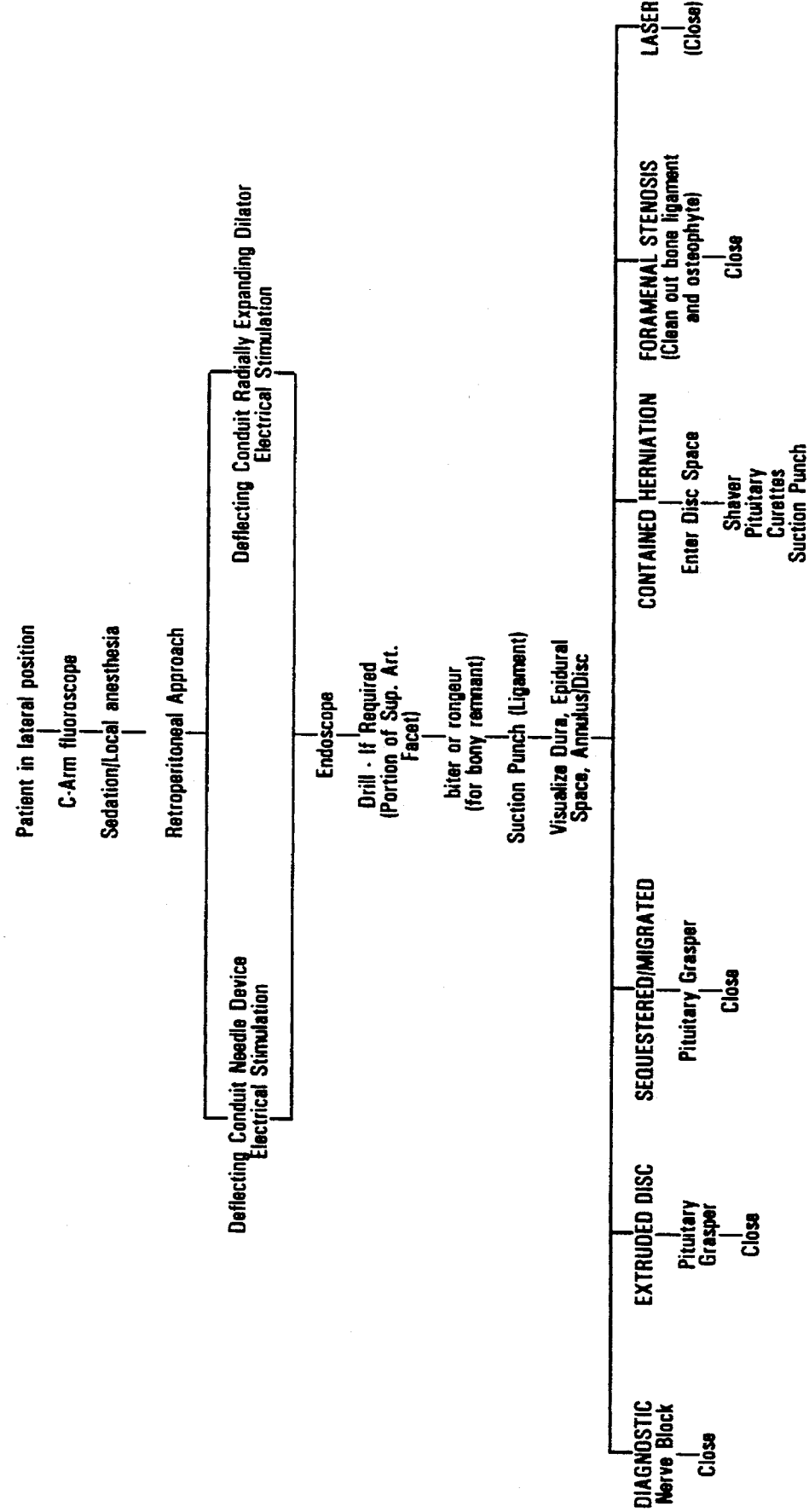

NERVE DEFLECTING CONDUIT NEEDLE AND METHOD

FIELD OF THE INVENTION

This invention relates to surgical tools and methods for back surgery. In particular, this invention relates to methods and devices for accessing the neural foramen in patients having a disc herniation or in patients with nerve root pain emanating from a vertebral foramen.

BACKGROUND OF THE INVENTION

There are a variety of pathological conditions which require surgical intervention in and around the spinal epidural space. The most common of these is intervertebral disc herniation. Other conditions which require surgical intervention in and around the epidural space include, but are not limited to, foramenal stenosis, tumor excision procedures including excision of neurofibromas, meningiomas, and the like, and procedures involving nerve root blocks.

The neural foramen provides an entry port into the epidural space. The foramen is circumscribed by the pedicles of adjacent vertebral bodies and the floor of the foramen is formed from the annulus of a disc positioned between adjacent vertebra. Disc herniations extend from the anterior surface of the epidural space, extending into the space or out of the neural foramen. There are currently three major routes for accessing herniated disc tissue: laminectomy and hemilaminectomy procedures, anterior approaches and posterolateral approaches.

Laminectomy and hemilaminectomy procedures are some of the more common procedures for treating herniated discs. These procedures allow direct access to the epidural space through the removal of all, or a portion, of the adjacent lamina (i.e. the posterior vertebral surface) to expose the nerve root and the disc herniation. These procedures are tedious and involve extensive dissection and surgical manipulation associated with the required bone excision. An added complication of these procedures is the threat of spinal instability resulting from excess bone removal.

In the posterolateral approach for accessing herniated disc tissue, exemplified by U.S. Pat. No. 4,573,448 to Kambin, the patient is positioned in a lateral decubitus or in a prone position. In this method, instruments are introduced into disc tissue at an angle of approximately 35° relative to the mid-sagittal plane of the patient (the longitudinal plane running perpendicular to the spine). Here, attempts are made to indirectly access the herniated tissue by entering disc tissue and excavating to the site of the herniation. Entry is complete when the surgical tools are positioned within the disc tissue anterior to the spinal epidural space. Once in position, the surgeon excavates through the disc tissue, at approximately a 60° angle, posteriorly, to the site of the herniation and removes the herniation from inside the disc, without entering the epidural space.

The Kambin procedure can be performed using one or two incision sites and requires steerable tools and angulated scopes. Because the method necessarily involves excavation of the disc tissue, there is significant motivation to keep the excavation as narrow as possible. The narrow opening requires successive entry and removal of endoscopic equipment and excavators thereby increasing the length of time of the surgical procedure. Normal disc tissue is destroyed and removed in this technique with the added complication that the surgeon cannot simultaneously view the area to be excised while excavation is taking place. The surgeon is also unable to see into the epidural space where the actual pathology lies unless a second incision on the opposite side of the spine is used, thereby permitting simultaneous visualization and excision of disc tissue.

U.S. Pat. No. 4,638,799 to Moore details a needle guide apparatus for positioning surgical instruments suitable for disc chemonucleolysis via a posterolateral approach. Like Kambin, Moore also contemplates indirect entry disc tissue to correct a disc defect. The needle guide fixes the angle of entry into disc tissue with preferred entry angles ranging from 45° to 55°. Neither Kambin nor Moore discloses a method for entering the spinal epidural space.

Anterior approaches to correct intervertebral disc herniation are generally an improvement over the posterolateral approach because the target herniation is in line with the entry port. As a result, the herniation is easier to visualize from within the disc tissue. However, anterior approaches typically require extensive insufflation of the peritoneal space. Where insufflation is not employed, entry into the peritoneum is complicated by the inherent risk that bowel or ureter tissue could be injured and such injury to the bowel can result in life threatening sequelae. Like the Kambin approach described above, the anterior approach also requires that the surgeon remove intact, normal disc tissue to get to the area of the herniation while the surgeon works from inside the disc space and the anterior approach does not permit direct visualization of the epidural space where the pathology lies. Therefore there remains a need in the medical arts for a surgical method and device which permits direct access and visualization of the epidural space without requiring extensive removal of bone or disc tissue.

In the aforementioned methods, there is the potential for complications resulting from the length surgery, patient recovery time and the risk of complications during the surgical procedure. Patient recovery time is further extended when the patient is of an advanced age. Since disc herniation is a degenerative pathology, it is not unexpected that the majority of individuals with disc herniations or other back complications requiring access to the foramenal space are of advanced age. For elderly patients, increased surgical time, general anesthesia and spine destabilization resulting from bone removal can all increase patient recovery time. Thus, there is a need for a surgical method that decreasing the length of surgery and reduces the length of patient recovery.

SUMMARY OF THE INVENTION

The methods and devices of the present invention facilitate access to the epidural space via the neural foramen without disturbing the integrity of the nerve roots and spinal dura while working with and around the anatomical features of the lateral surfaces of the spinal column. Unlike the above described prior art techniques, the methods and devices of the present invention are designed to gently deflect the neural roots away from the foramenal space.

In one aspect of this invention, a deflecting conduit needle device is disclosed. The device preferably embeds in disc tissue adjacent to the neural foramen associated with the spinal defect. The anchored device provides a conduit to connect the retroperitoneal space with the spinal epidural space. In one embodiment, the device includes a transverse conduit through which secondary surgical instrumentation is introduced at an angle to directly access the anterior surface of the epidural space. In this embodiment the sum of the angle of insertion of the deflecting conduit needle device and the angle of the transverse conduit relative to the longitudinal axis of the device is at least 70°.

In a second embodiment of the deflecting conduit needle device, the device forms a hollow sleeve along the longitudinal axis of the device allowing secondary surgical instrumentation to be introduced into the hollow sleeve and exiting at the transverse conduit adjacent the neural foramen.

In another aspect of the invention, the deflecting conduit needle device is modified to function as a radially expanding dilator. This modified device is equipped with a central needle guide and an expandable sleeve. Again, the device may be formed with a transverse conduit and/or as a hollow sleeve exiting at the location of the transverse conduit adjacent the relevant neural foramen.

In yet another aspect of the invention, the device is modified as a "peel away" catheter and includes an outer peelable sleeve.

The invention also relates to a method for directly accessing the epidural space via the neural foramen. In one embodiment, the method includes accessing the space using one of the disclosed deflecting conduit needle devices and in another embodiment, the method provides direct access to the epidural space via the neural foramen. In one preferred method, the deflecting conduit needle device is positioned, based on an anterior fluoroscopic view, lateral to the medial aspect of the pedicle base and is positioned such that it abuts a line defined by the posterior aspect of the vertebral body and the disc based on a lateral fluoroscopic view. The device is embedded into the disc tissue at its distal tip and rotated about 45° to deflect the nerve root extending from the neural foramen and to align the transverse conduit of the device with the neural foramen. Secondary surgical instrumentation is introduced through the transverse conduit to access the epidural space via the neural foramen.

BRIEF DESCRIPTION OF THE DRAWINGS

FIG. 9 is a cross-section of a patient mid-section with the deflecting conduit needle in place;

FIG. 11 is a flow diagram illustrating a preferred surgical method according to this invention.

DETAILED DESCRIPTION OF THE INVENTION

The present invention relates to a method and a deflecting conduit needle device for connecting the retroperitoneal space to the spinal foramen, and in particular for accessing the anterior and lateral portions of the spinal epidural space.

The terms "spinal foramen", "neural foramen" and "foramenal space" are used interchangeably throughout this document.

The term "entering" is used herein to include any surgical technique for accessing an internal body space in a patient through a surgically created opening. Thus, the term "entering" includes the use of incisions, punctures, or the like.

The device and method of the present invention have a variety of surgical applications. Not only is the device suitable for treating disc herniation, but it may be used to directly treat foramenal stenosis, excise nerve tumors, or to perform diagnostic nerve blocks. As one embodiment of this invention, a deflecting conduit needle device is employed to gently deflect the nerve root away from the neural foramen formed between adjacent vertebral pedicles while simultaneously increasing the angle of entry into the foramenal space to between 70° and 90° and more preferably between 75° and 80° relative to the mid-sagittal plane of the patient while employing a retroperitoneal approach.

Figure 1:
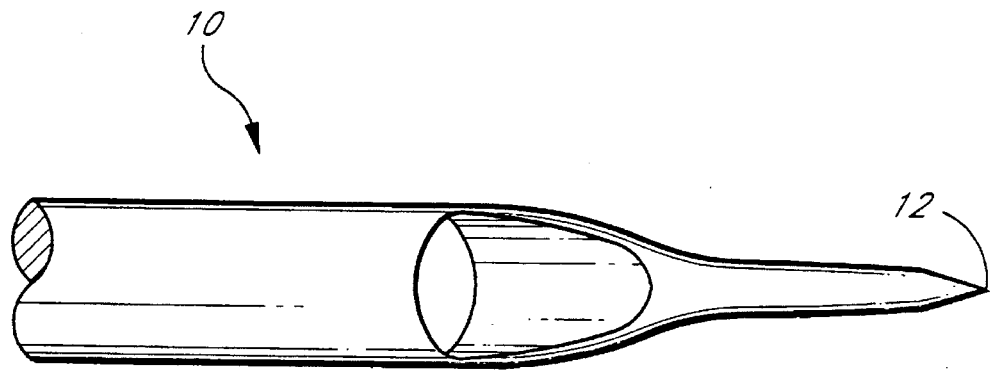
FIG. 1 is an anterior view of the distal portion of a preferred embodiment of the deflecting conduit needle of the present invention.
Figure 2:
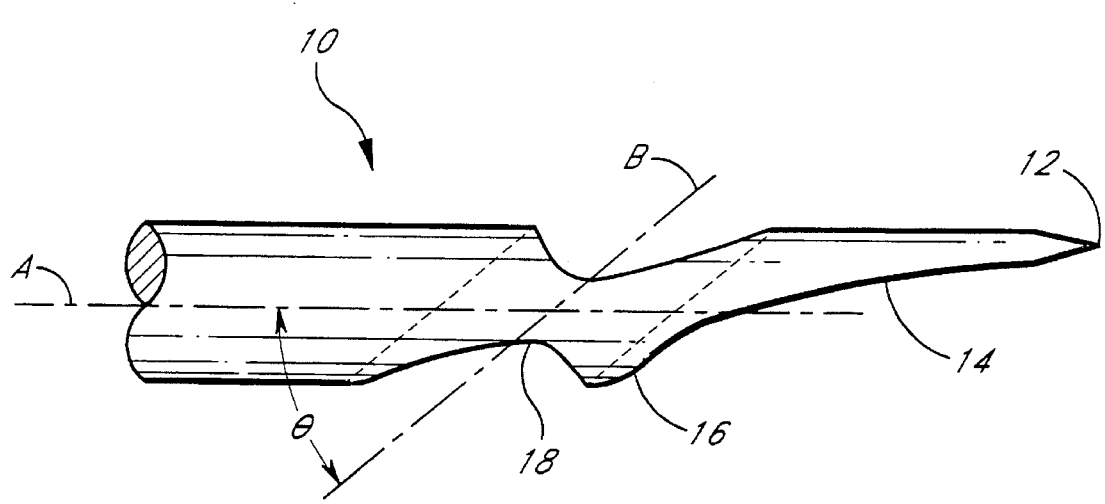
FIG. 2 is a lateral view of the distal portion of a preferred embodiment of the deflecting conduit needle of the present invention.
Figure 3:
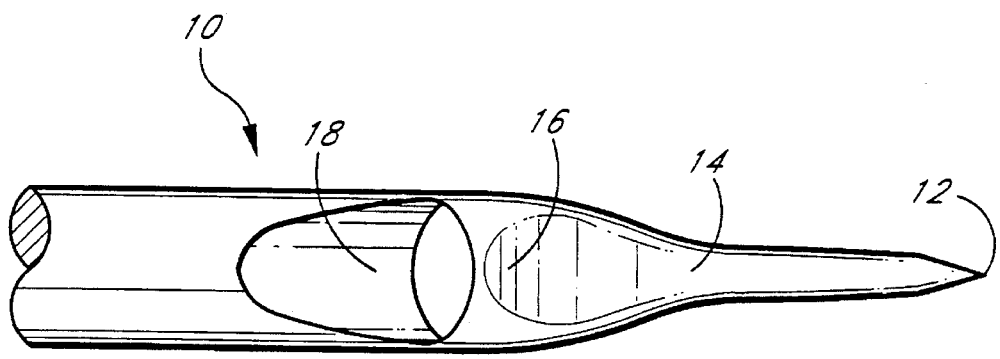
FIG. 3 is a posterior view of the distal portion of a preferred embodiment of the deflecting conduit needle of the present invention.

Referring to FIGS. 1–3, the preferred deflecting conduit needle device of this invention has a substantially elongate body 10 which includes a proximal end and a distal end, with the proximal end closest to the surgeon and the distal end positioned adjacent to the neural foramen. The elongate body 10 extends substantially along a first axis (axis A). The body of the device may be substantially cylindrical or it may have a variety of other cross-sectional shapes. Further, the shape of the deflecting conduit needle device, while substantially elongate, may optionally be provided with a variety of out-pouchings, curves, or the like.

In a preferred embodiment of the invention, the distal portion of the device terminates in a pointed tip 12. The tip is sufficiently sharp to permit the device to puncture the annulus fibrosis of the disc in question. The device has, at its distal end, an anterior and a posterior face. FIG. 1 diagrams the anterior face of the device. As is readily appreciated from FIG. 1, the pointed tip 12 widens slightly, preferably reaching the full circumference of the device within the distal one eighth of the length of the device and more preferably within the distal three centimeters of the device.

Referring now to FIG. 2 and to FIG. 3, in a preferred embodiment of the device, the posterior surface of the distal end of the device is bevelled relative to the anterior surface. This bevelled surface 14 is preferably a continuous surface with smooth rounded edges, unlike a needle used for venipuncture. The bevelled surface 14 widens from or adjacent to the tip 12 to a heel 16 located at the proximal end of the bevelled surface 14. The preferred contour of the bevelled surface 14 can be readily appreciated from the lateral view of the distal portion of the device, illustrated in FIG. 2.

In this preferred embodiment, the elongate body of the device 10 includes a transverse conduit 18 extending through the device. The conduit traverses the elongate body 10 at substantially a second axis (axis B) relative to the first axis (axis A) of the elongate body, such that an acute angle ($\theta$) is formed between the first axis and the second axis. The acute angle is preferably between 25° and 55° and more preferably between 30° and 40° with a preferred angle of about 35°. However, even those of ordinary skill in the art will recognize that the transverse conduit 18 within the elongate body 10 can be positioned at a variety of angles relative to the axis formed by the elongate body and that the ultimate angle of the conduit 18 will depend on the preferred angle of entry of the device relative to the mid-sagittal plane of the patient. Preferably, the sum of the angle of introduction of the device relative to the mid-sagittal plane of the patient and the acute angle formed between the first axis and the second axis is at least 70°.

To continue, the conduit 18 traverses the elongate body within a range of distances as measured from the distal tip of the apparatus. In a preferred embodiment, the conduit is positioned within the distal one-eighth of the device and in another embodiment, the conduit is positioned within four centimeters from the tip and is preferably positioned proximal to the bevelled surface 14 and adjacent to the heel 16 of the bevelled surface 14 of the device.

Figure 10A:
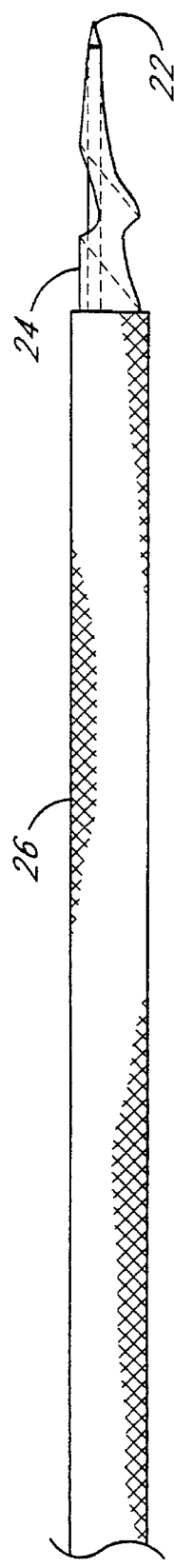
FIG. 10 is a lateral view of a deflecting conduit needle dilator embodiment.
Figure 10B:
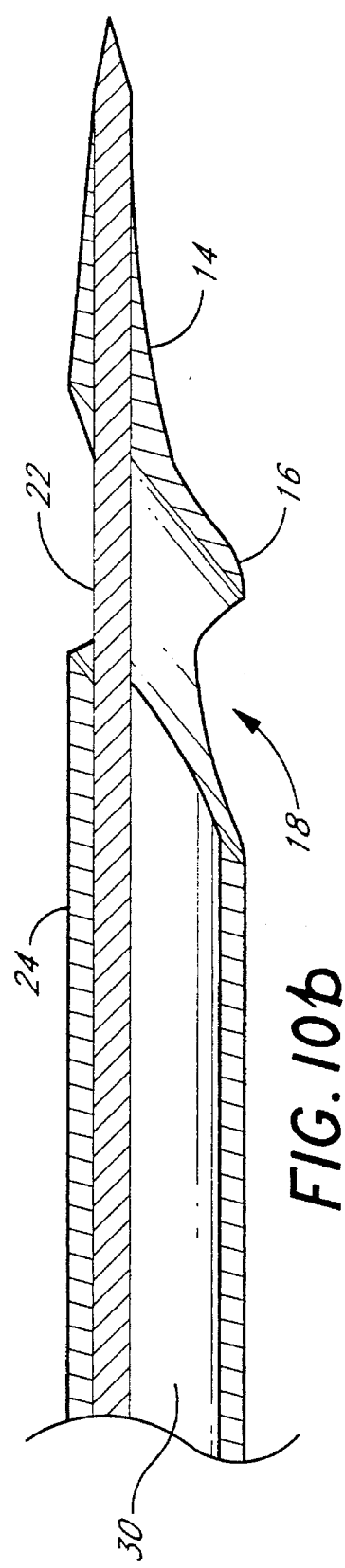
Figure 10C:
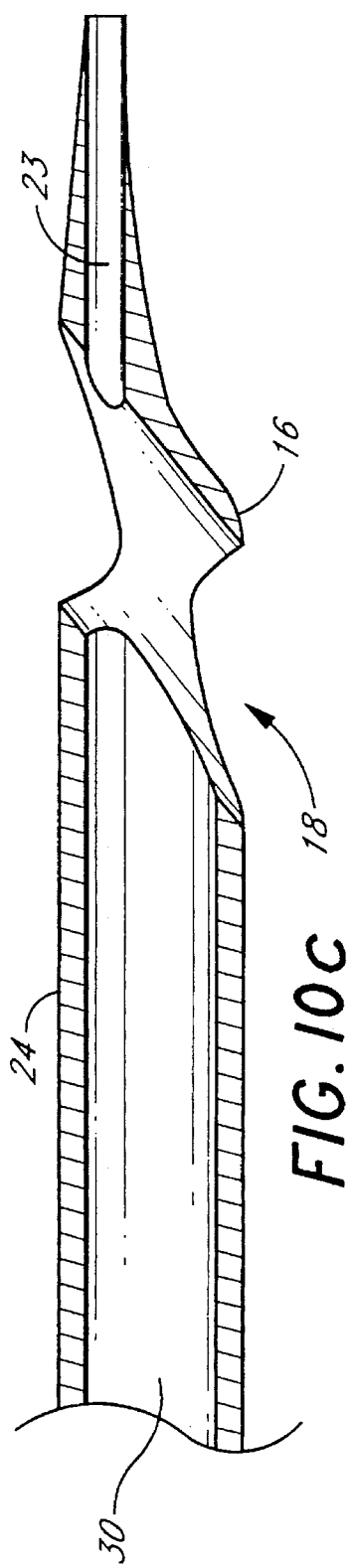

In one embodiment of this invention, the elongated body of the device is hollow along its longitudinal axis with the hollow interior cannula 30 portion communicating with the transverse conduit 18 as illustrated in FIG. 10c. In this embodiment, the device forms a hollow sleeve such that the proximal end of the device forms a first opening and extends through the device terminating at the conduit 18. Thus, surgical instruments can be introduced through the conduit 18 or through the hollowed proximal portion of the device and in both instances, the instruments exit the conduit 18 from the anterior surface of the device.

In a preferred embodiment of this invention the effective length of the elongate body 10 of the device is preferably between 10 cm and 45 cm in length. The deflecting conduit needle device can be held by the surgeon or assistants throughout the surgical procedure, or the device can be mounted or stabilized on a surgical stand, or the like. Moreover, while a posterolateral approach is preferably disclosed in Example 1, those skilled in the art will recognize that the disclosed device could be readily employed in surgical procedures using other surgical approaches. Therefore, the length of the device will vary depending on how it is employed in a particular surgical procedure. Where the device is held by the surgeon in a posterolateral procedure, the deflecting conduit needle device is preferably between 17 cm and 21 cm, in one embodiment length, and in another preferred embodiment, the deflecting conduit needle device is between 25 cm and 31 cm in length.

The cross-sectional dimensions of the device will also vary, with the overall width of the device depending on whether or not the device forms a hollow sleeve for the introduction of surgical tools to the disc site or whether the device is solid and lacking an accessible longitudinal sleeve. For deflecting conduit needle devices without a central accessible hollow sleeve, the device will preferably have a cross-sectional dimension of between 4 mm to 10 mm and preferably between 8 mm to 10 mm.

The transverse conduit 18 is positioned to accommodate instrumentation suitable for performing the types of surgical techniques which require access to the anterior and lateral portions of the spinal epidural space. Thus, the transverse conduit 18 will be suitable to accommodate endoscopes, trocars, rongeurs, cannula sleeves, arthroscopic shaver blades, suction devices, cauterizing tools, and the like. In a preferred embodiment, the transverse conduit 18 has a cross-sectional dimension of at least 2.0 mm and preferably between 5 mm to 9 mm. Where the elongate body 10 is cylindrical, the transverse conduit will preferably have a cross sectional dimension of 0.5 mm to 2.0 mm less than the cross-sectional dimension of the elongate body 10. In this preferred embodiment, the transverse conduit, like the shape of the elongate body 10, is substantially cylindrical; however, the transverse conduit, like the cross-section of the elongate body, may also have a variety of other shapes. Thus, where the cross-sectional shape of the device is circular, an oblong conduit will be useful for maximizing the working space for accessing the spinal epidural space via the neural foramen.

The deflecting conduit needle device can be prepared from any number of materials well known in the surgical arts. These include, for example, surgical steel, other suitable surgical alloys, TEFLON®, or related materials, or thermoplastic polymers including polypropylene, polystyrene, polyvinylchloride, silastics or the like, including other materials which can be sterilized for surgical use. Those skilled in the art of surgical device manufacture will be able to select a suitable material.

FIG. 9 depicts a mid-section of a patient with a deflecting conduit needle device 10 in place. In a preferred method of this invention, the patient is positioned in a lateral position and the peritoneum is insufflated as illustrated in FIG. 9. Minimal insufflation through an insufflation port 46 into the retro-peritoneal space 48 is preferably used to retract the peritoneum 34 containing the bowel 36. Those skilled in the art will recognize that the extent of insufflation needed to access the spinal foramen will vary between patients. Thus, FIG. 9 is illustrative and is not intended to demonstrate the extent of insufflation required to perform the claimed technique.

Figure 4:
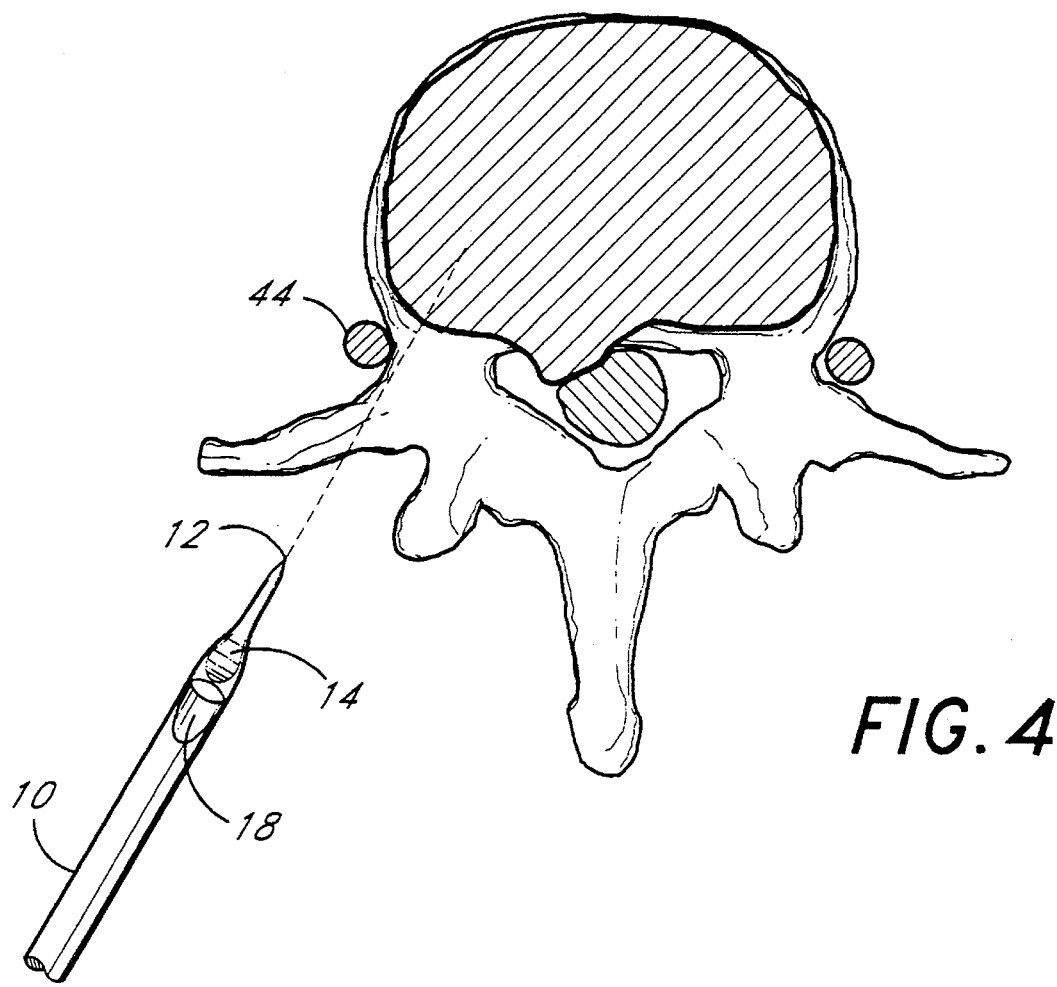
FIG. 4 is a cross-section of a vertebra illustrating the positioning of the device in a method of using the deflecting conduit needle of FIG. 1.

Once insufflation is completed, puncture or incision is made in the retroperitoneum. The preferred entry position of the deflecting conduit needle device 10 is illustrated, relative to the patient mid-section in FIG. 9. FIG. 4 illustrates the preferred angle of entry and position of the device as it approaches the spinal column. Preferably, the deflecting conduit needle device 10 is inserted through a retroperitoneal percutaneous puncture and advanced toward the foramenal space in need of surgical intervention. Using fluoroscopy, and referring to FIG. 4, the distal tip 12 is guided toward the disc space in need of surgical intervention. The device tip 12 is preferably positioned, based on an anterior view, lateral to the medial aspect of the pedicle base. Based on a lateral view, the needle tip is positioned such that it abuts a line defined by the posterior aspect of the vertebral body and the disc. The posterior surface of the device, as illustrated in FIG. 3, faces rostrally as the device moves into position. Once in position, pressure is applied to the distal tip 12 which is sufficiently sharp such that the device is embedded in the disc annulus. Care is taken such that the device impales the disc annulus without damaging adjacent nerve roots associated with the neural foramen. The angle of entry and the angle that the device is embedded into the disc annulus relative to the mid-sagittal plane C, as shown in FIG. 9, is important to facilitate easy access to the epidural space via the neural foramen. Preferably, for lumbar procedures, the device is positioned at a 35° to 55° angle relative to the mid-sagittal plane of the patient.

Figure 5:
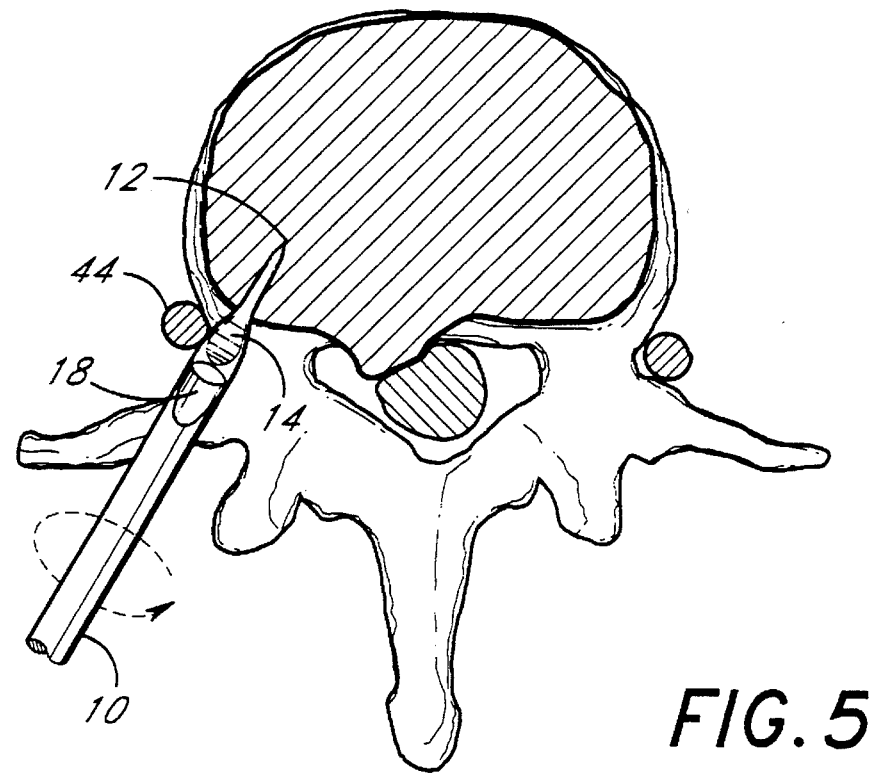
FIG. 5 is a cross-section of a vertebra illustrating the nerve deflecting step in the method of using the deflecting conduit needle of FIG. 1.
Figure 6:
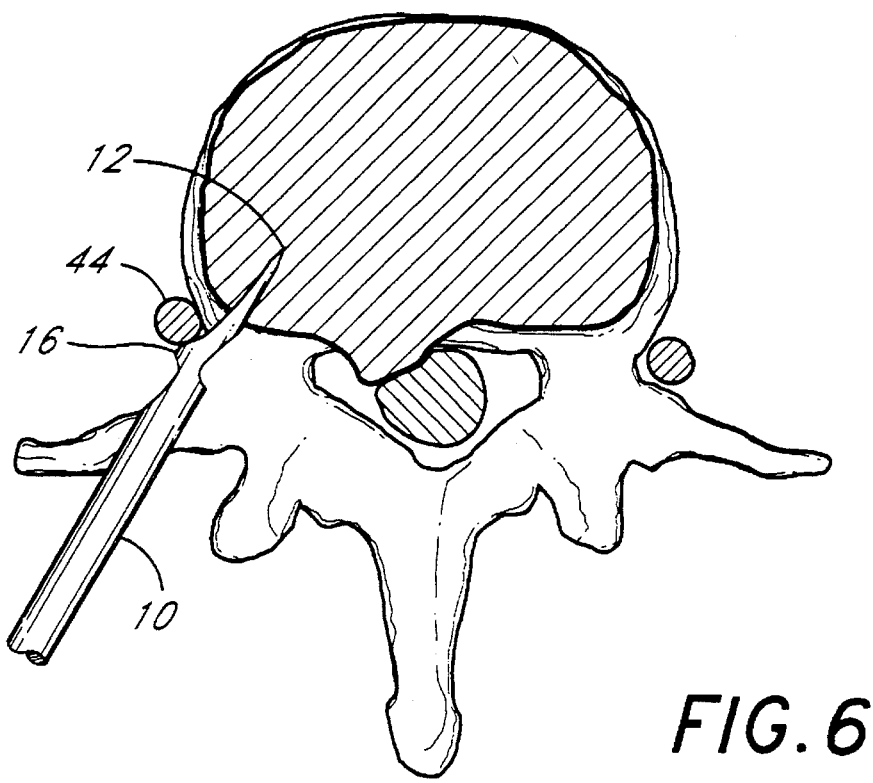
FIG. 6 is a cross-section of a vertebra illustrating the deflecting conduit needle of FIG. 1 positioned in disc tissue.

As illustrated in FIG. 5, once the deflecting conduit needle device 10 is embedded in the disc annulus, the device 10 is gently rotated about 45° clockwise if treating the right side of the patient and 45° counterclockwise if treating the left side of the patient. The rotation of the heel 16 of the bevelled surface 14 gently deflects the nerve root 44 away from the foramenal space, permitting easier and safer access to the foramenal space and aligns the transverse conduit 18 with the neural foramen. The position of the device following rotation is provided in FIG. 6. The deflecting conduit needle device 10 is now in place, connecting the retroperitoneal space with the spinal epidural space.

Figure 7:
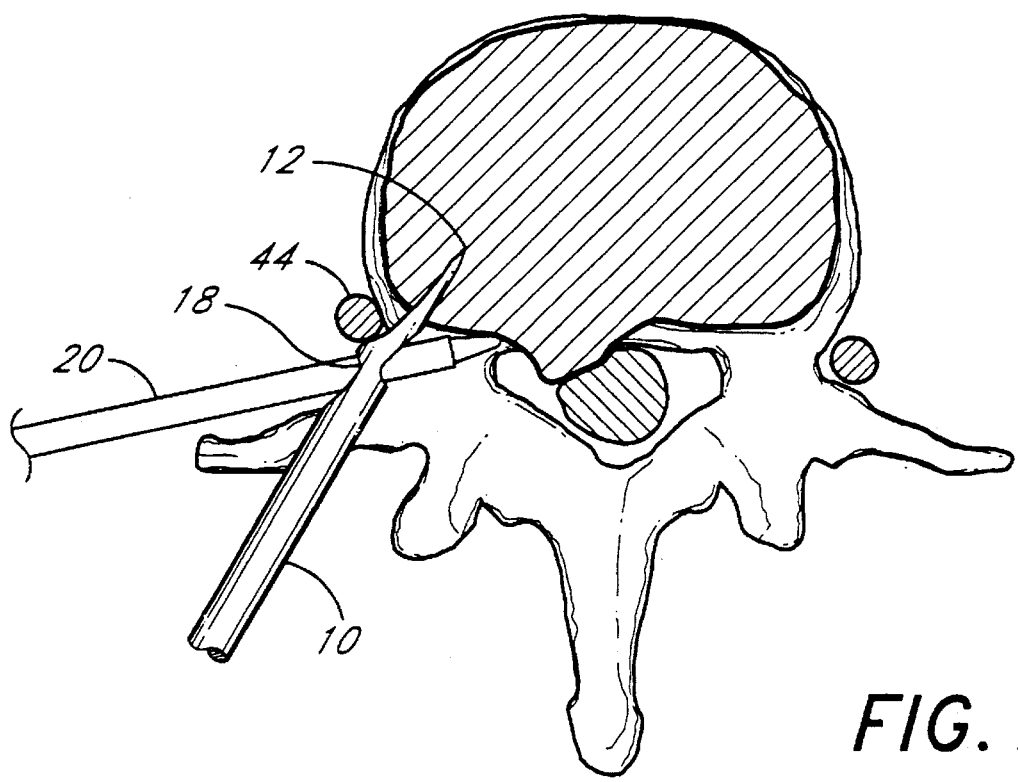
FIG. 7 is a cross-section of a vertebra illustrating the deflecting conduit needle of FIG. 1 positioned to receive surgical instrumentation to access the posterior surface of the foramenal space.

Next, referring to FIGS. 7 and 9, secondary surgical instrumentation 20 suitable for performing the discectomy or other procedures associated with accessing the spinal foramen are introduced either using the same incision or through a second incision site 42 through the transverse conduit 18 and into the foramenal space and preferably into the anterior and lateral portions of the spinal epidural space. A secondary puncture is preferably introduced into the patient along the flank. First, a fluoroscope grid is positioned on the flank to align the puncture site with the conduit 18. Once the angle of entry is identified, secondary surgical instrumentation, including initially, a needle or canula are introduced through the puncture to the conduit 18. Electrical stimulation is preferably employed to ensure that the nerve root 44 has been deflected away from the foramen before the secondary instrumentation 20 fully engages the transverse conduit 18.

Once the needle is in place, a canula can be dropped over the needle and slidably positioned adjacent the foramen. Secondary surgical instrumentation required to perform the discectomy or other surgical procedures are advantageously introduced through the canula. The transverse conduit serves as a guide for maintaining an angle suitable for accessing the spinal epidural space via the neural foramen. An exemplary detailed surgical method employing the device of this invention is provided in Example 1.

Figure 8:
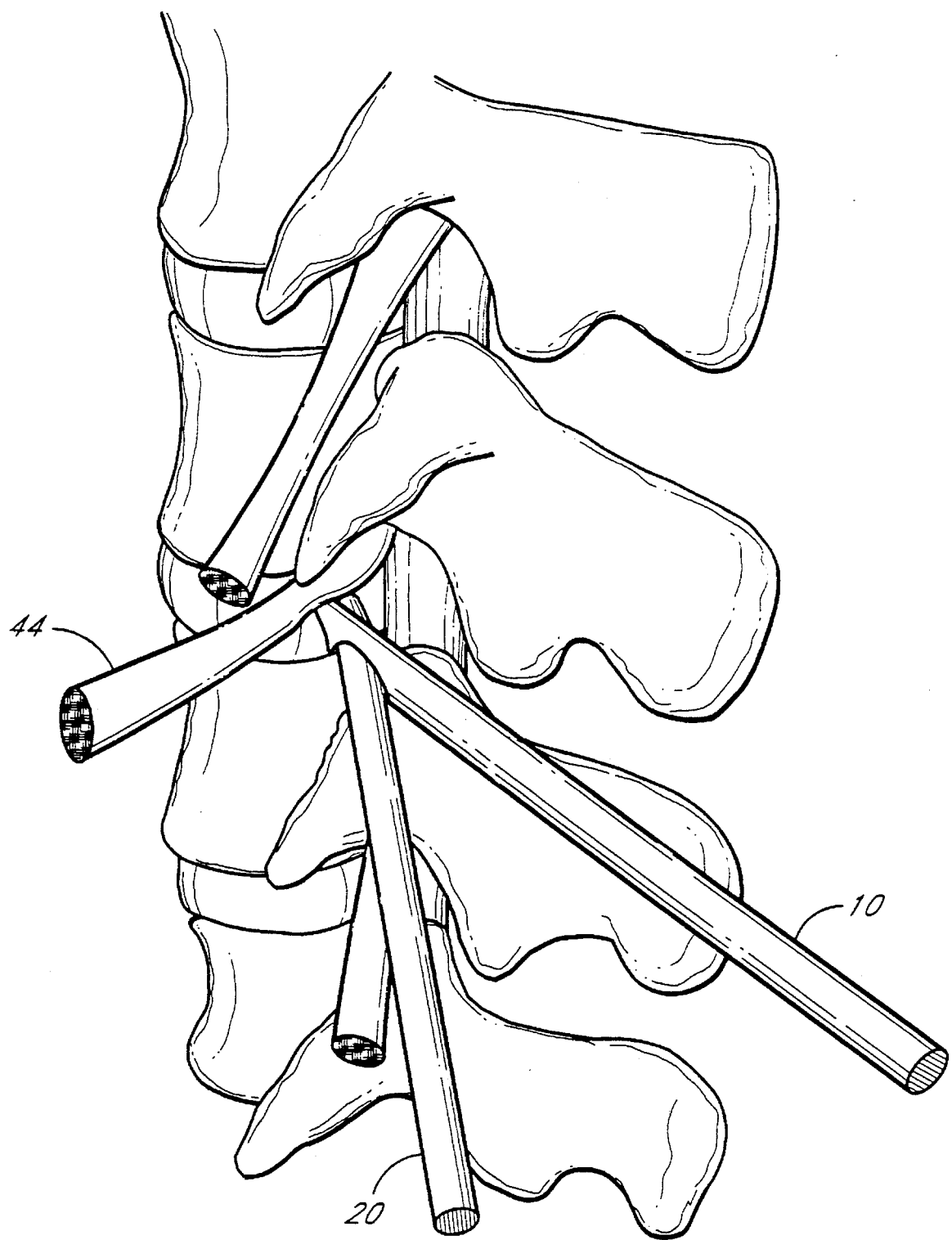
FIG. 8 is a lateral view of the vertebral column with surgical instrumentation positioned in the transverse conduit of the device of FIG. 1.

FIG. 8 provides a lateral view of the device 10, in position, with the nerve root deflected with the device 10 receiving secondary surgical instrumentation 20 such as a cannula or endoscope suitable for use with other surgical instruments such as suction punches, rongeurs, and the like.

While this method uses two entry sites, it is also contemplated that one entry site can be used in some cases. For example, it is possible with the use of fluoroscopy, real time imaging with ultrasound, magnetic resonance imaging guidance or computerized axial tomographic guidance to directly access the epidural space through the neural foramen without the deflecting conduit needle device. A single entry site procedure can also be performed using the deflecting conduit needle device 10. For a single entry site procedure the deflecting conduit needle device is preferably hollow from the proximal end to the transverse conduit 18 such that secondary surgical instrumentation 20 can be inserted through the hollow passageway and exit through the transverse conduit. In this embodiment, steerable surgical equipment guided through the length of the body 10, out the transverse conduit 18 and into the epidural space via the neural foramen.

An important benefit of the present device, as compared with the prior art, is that the device provides a method of increasing the angle of entry into the foramenal space from what is disclosed to at least 70°, without requiring extensive retroperitoneal insufflation. The angular position of the deflecting conduit needle device 10 relative to the mid sagittal plane of the patient and the angle of the transverse conduit, in combination with nerve deflection, provides a substantially lateral approach for discectomy. The technique is minimally invasive while providing direct visualization of the site in need of surgical intervention.

In another modification of the deflecting conduit needle device, the device includes a blunt distal tip, as shown in FIG. 10c. In this embodiment, the device is not embedded in disc tissue, rather the device is brought into position and held in place by external supports such as the support disclosed in U.S. Pat. No. 4,638,799 to Moore. Alternatively, the device can be held in place by the physician or surgical assistants.

It is further contemplated within the scope of this invention that the deflecting conduit needle device can be modified to function as a dilator. Tools for dilating the access site during a surgical procedure are well known in the art. One such tool is a radially expanding dilator (RED). This type of device is disclosed in U.S. Pat. Nos. 5,312,360 and 5,275,611 to Behl which are both hereby incorporated by reference. Such devices are suitable for enlarging percutaneous penetrations in body cavities and include elongate guide members and at least one elongate dilatation member. The central portion of the guide member is removed once the device is positioned within a body cavity and a unitized dilator is introduced to widen the cross-sectional diameter of the device. This permits surgical instrumentation to be introduced through the device to facilitate the surgical procedure while minimizing the invasiveness of the procedure.

The deflecting conduit needle dilator embodiment of this invention can be used in association with the first puncture or alternatively, the dilating needle can be employed in the second step to facilitate introduction of surgical instrumentation through the conduit 18. Referring to FIG. 10a, in the first dilation embodiment of this device, the device has a proximal end and a distal end and comprises a central needle guide 22, an elongate deflecting dilator 24 and an expandable outer sleeve 26. The expandable outer sleeve 26 may be prepared from a variety of materials known in the art, including but not limited to rubber, heat-stable polymers, or woven sleeves prepared from polymers or other suitable material. Other suitable materials are disclosed in U.S. Pat. Nos. 5,312,360 and 5,275,611 to Behl. The elongate deflecting dilator optionally comprises a transverse conduit 18, a hollow interior cannula 30 and a deflecting heel 16 with a bevelled surface positioned between the distal end and the heel 16. The hollow interior cannula 30 is just wide enough at the distal terminus to accommodate the central needle guide. The transverse conduit 18 traverses the apparatus and is positioned along the distal one-eighth of the device. The hollow interior cannula 30 is preferably wide enough at the proximal end to accommodate both the central needle guide 22 and steerable surgical equipment including secondary surgical instruments 20, such as endoscopes, trocars, arthroscopic shavers, rongeurs and the like, and the cannula 30 preferably communicates with the transverse conduit 18 such that surgical equipment introduced at the proximal end of the device can be passed down the cannula 30 and exit at the transverse conduit 18.

During use the central needle guide 22 with the expandable sleeve 26, is introduced into the patient using the procedures disclosed in Example 1. The needle 22 impales the disc annulus at a position medial to the exiting nerve root. Once positioned within the disc annulus, the elongate deflecting dilator 24 is positioned over the central needle guide 22, within the expandable outer sleeve 26 as illustrated in FIG. 10b. In this embodiment, the elongate deflecting dilator serves to expand the diameter of the expandable outer sleeve from within. This type of expansion is safer for the nerve root. Once in place, the device, can be rotated 45° to deflect the nerve root. The central needle guide 22 is removed, as illustrated in FIG. 10c, and instruments are introduced down the central longitudinal axis of the dilator using a steerable endoscope. If it is impossible to access the epidural space by this route, the surgeon can make a second puncture in the flank of the patient and introduce surgical instrumentation through the transverse conduit 18, into the epidural space via the neural foramen.

In a second dilator embodiment, the dilator is introduced through the transverse conduit 18 of the deflecting conduit needle device 10, as illustrated in FIG. 1. In this embodiment, a probe rather than the needle guide 22, is inserted with an expandable sleeve 26 through the second puncture, in line with the transverse conduit and positioned adjacent to the neural foramen. Once in position, the dilator is introduced within the expandable sleeve and the probe is removed. This serves to gently increase the cross-sectional diameter of the device to provide greater access to the epidural space with minimal invasiveness.

The devices of this invention can also be modified as a "peel away" catheter. "Peel away" catheters are known in the art such as those described in U.S. Pat. No. 4,581,025 and are available from Cook Group Company (PEEL-AWAY® catheter, Bloomington Ind.) or from Boston Scientific Corporation (BANANA PEEL®, Medi-tech, Boston Scientific Corporation, Watertown, Mass.).

In this embodiment, the secondary surgical instrumentation is a "peel away" cannula, introduced through transverse conduit 18. The "peel away" portion of the device is an outer sleeve which can be peeled away. The sleeve forms a cannula. A needle is aligned with the transverse conduit 18 of the deflecting conduit needle device 10 which is anchored within the disc annulus. Once the needle is in place, the "peel-away" sleeve and inner styler are slidably positioned over the needle. The needle is retracted and endoscopes and other surgical instrumentation are introduced through the sleeve. If needed, the sleeve can be peeled away as is provided in either the PEEL-AWAY® or the BANANA PEEL® sleeves disclosed above.

Methods for preparing these modified embodiments will be readily apparent to those skilled in the art in view of this disclosure. Thus, it is contemplated that these modifications and others, which include the inventive features of the device, can be prepared without undue experimentation.

FIG. 11 provides a flow-diagram of a surgical method for accessing the epidural space via the neural foramen. The flow-diagram indicates that the patient is preferably positioned in the lateral position with a C-arm fluoroscope positioned to facilitate visualization of the deflecting conduit needle device positioning steps of this invention. The patient is sedated and the retroperitoneum is gently insufflated, as needed, to displace abdominal viscera out of the way of the needle tracts. The retroperitoneal approach, as disclosed in FIG. 11 employs either the deflecting conduit needle device or the deflecting conduit radially expanding dilator device. The positioning steps associated with using these devices are discussed above with reference to FIGS. 4–9. Electrical stimulation is used to ensure that the nerve tissue is deflected away from the foramen and is not blocking that portion of the transverse conduit that is adjacent to the neural foramen. An endoscope is introduced through the transverse conduit of the device or alternatively, in the hollow interior cannula embodiment the instrument is introduced down the proximal length of the device. Other instruments are introduced through the device including a drill (to remove a portion of the superior articulating facet) such as provided by Dyonics (Andover, Mass.), a biter or rongeur (to remove bony remnant) and a suction punch (to remove ligament), as needed, to access the epidural space via the neural foramen. Bone and ligament blocking access to the epidural space are removed so that the dura, the epidural space and the disc with its annulus can be visualized.

Once this region is visualized it is possible to treat extruded, sequestered/migrated or contained herniations. For extruded and sequestered/migrated herniations, a pituitary grasper is used to remove the disc tissue. For contained herniations, the disc space is entered and shavers, curettes and suction punches are used to remove the disc tissue. Using this method it is also possible to perform a diagnostic nerve block test or treat foramenal stenosis. During the treatment of the foramenal stenosis bone, ligament and osteophyte are removed. Alternatively, this method is suited to laser surgeries. Laser surgery procedures are known to those skilled in the art.

As has been discussed, the deflecting conduit needle device is useful for directly accessing the epidural space, via the neural foramen, without extensive bone dissection. The techniques taught herein advantageously employ a surgical approach requiring only local anesthesia. Moreover, the technique is minimally invasive and can be performed with a single, or preferably two small punctures. Further, the techniques disclosed in this invention accommodate the use of a wide range of surgical tools. In contrast to the anterior approach, which requires gross abdominal insufflation to avoid penetration or injury of the abdominal viscus, the present technique uses only minor insufflation of the retroperitoneal space.

In addition, the method of the present invention, unlike the posterolateral approach or the anterior approach, employs a straight line of entry to the site of disc herniation without disc excavation. This straight line of entry makes extensive manipulation with steerable surgical tools unnecessary and permits visualization of the spinal epidural space where the pathology lies. The present method is less invasive, since disc tissue dissection is not required and the method is safer because the lateral approach combined with insufflation reduces the likelihood that the ureter or abdominal viscus will be injured. Moreover, where nerve root compression is associated with the herniation, the methods of the present invention permit direct visual confirmation of the extent of the decompression. Direct access and visualization are not possible in any of the aforementioned prior art techniques.

A further benefit of the present invention over what is currently available in the art is that excavation or removal of intact disc tissue is not required to access the area of the epidural space containing the disc herniation. Other procedures requiring disc excavation or extraction run the risk that the disc space will settle, resulting in secondary pain. An additional complication of disc excavation is that the excavated disc may become unstable due to the removal of the disc material. Using the present technique, access to the epidural space does not depend on disc excavation, consequently there is no risk of disc destabilization. In further contrast to standard laminectomy procedures, the present invention does not require dissection of large amounts of bone to access the epidural space. This has the added benefit of reducing the risk of spinal instability as a result of the surgical procedure.

Importantly, the devices and methods of this invention are minimally invasive. Therefore, as will become apparent from a description of the surgical procedure of Example 1, and FIG. 11, the device of this invention permits the surgeon to correct the spinal defect while the patient is under local anesthesia. Further, the device offers flexibility not available in the aforementioned methods. The device of this invention and methods that employ direct access to the epidural space via the neural foramen facilitate discectomy procedures, foramenal stenosis correction procedures, tumor extractions or nerve root block procedures can be readily corrected using the procedures and devices disclosed herein on an outpatient basis.

The following example discusses a particular embodiment in detail and FIG. 11 discloses select surgical variations contemplated within the scope of the invention. There are a variety of other instruments and procedures which can accompany this technique and which are available to those of skill in the art. Thus, additional instrumentation and procedures would similarly permit one to successfully perform the intended methods of this invention.

EXAMPLE 1

Foramenal Approach for Lumbar Discectomy

The patient is placed in the lateral position with the symptomatic side up. The axilla on the underside of the patient is padded and the patient is affixed in a true lateral position as seen on fluoroscopy using a C-arm fluoroscope (OEC Medsystems, Inc. Salt Lake City, Utah). The procedure is carried out preferably under local anesthesia with strong sedation or, alternatively, with general anesthesia.

A retroperitoneal incision is made into the flank on the upper side of the back using a 10 to 12 mm incision into the retroperitoneal space. A dissecting balloon such as the Origin balloon, or the like, (Origin Balloon, Origin Medsytems, Inc. Menlo Park, Calif.) is inflated while endoscopy is being carried out. The balloon is removed and a trocar is introduced into the incision. Insufflation is carried out with a pressure as small as 5 psi.

At this point, a deflecting conduit needle device, as disclosed in FIG. 1, is inserted via a traditional posterolateral approach. The needle is placed into the disc space under fluoroscopic control. The device pierces the annulus lateral to the medial aspect of the associated pedicles and medial to the nerve root which has exited from that respective foramen. Once this position is established, the needle is rotated 45° clockwise or counterclockwise depending on whether the procedure is performed right or left of the midline. The angle of entry of the deflecting conduit needle device combined with the angle of the conduit within the device provides a nearly full lateral approach relative to the anterior-posterior dimension so that entry into the foramen will be nearly a full lateral trajectory. In this position, the conduit serves to connect the retroperitoneal space with the epidural space of the spinal canal.

Rotation of the needle by 45° laterally displaces and retracts the nerve root which has exited from the foramen. Using lateral fluoroscopy, the conduit is located so that its maximal dimension becomes apparent.

The surgeon makes a lateral puncture (preferably between 8 cm and 10 cm) in the flank in line with this conduit as seen on fluoroscopy, preferably using a 6.5 mm needle. In this example, the needle is a silastic access trocar. Both the needle and cannula catheter are produced by Cook Instruments (Bloomington, Ind.). Once the access catheter has engaged the lateral aspect of the conduit in the deflecting conduit needle device, the surgeon removes the inner trocar of the access catheter and inserts an endoscope with working port down the catheter, in effect, cannulating the conduit, through the transverse conduit of the deflecting conduit needle device. This procedure is performed fluoroscopically and/or using a laparoscope inserted in the retroperitoneal space.

Once positioned, visualization is possible by the endoscope. The endoscope can be a rigid rod lens system or a steerable fiberoptic device. Preferably a 4 mm working port endoscope is used with light source and optics. The scope has suction and irrigation ports at its distal end allowing simultaneous suction and irrigation.

Upon entering the foramen with the endoscope, the surgeon explores the epidural space. The surgeon can drill off a portion of the bony lateral foramen, that is, the lower portion of the superior articular facet, if it is blocking access to the foramenal space. This permits visualization of the lateral aspect of the spinal dura along with the nerve root and epidural space containing blood vessels, fibrous tissue and fat.

The annulus of the disc space with its herniation is also visualized and the surgeon can remove the herniation directly without entering the disc space if the herniation is an extruded fragment. It is now also possible to puncture the annulus to enter the disc space to pursue a herniation contained within the annulus. Automated shavers, suction punches and rongeurs are used to remove the contained disc herniation. Next, the epidural space is again examined to ensure that the disc herniation has been removed in its entirety.

When the removal procedure is completed, the trocars are removed and the entry site is sutured. Steri-Strips are applied to the skin. The patient is taken to the recovery room for observation and is discharged two to three hours postoperatively.

While particular embodiments of the invention have been described in detail, it will be apparent to those skilled in the art, that these embodiments are exemplary rather than limiting, and the true scope of the invention is that defined in the following claims.

What is claimed is:

1. A surgical apparatus for accessing the spinal foramen comprising:

an elongate body extending substantially along a first axis with a cross-sectional diameter of at least 3.0 mm, said body having a proximal end and a distal end, said distal end comprising a tip that is sufficiently sharp to puncture disc tissue thereby anchoring said apparatus in said tissue, and a conduit having a cross-sectional diameter of at least 2.0 mm positioned along the distal one-eighth of said body, said conduit extending substantially along a second axis and traversing said apparatus, said second axis positioned at an acute angle relative to said first axis.

2. The apparatus of claim 1, wherein said distal end further comprises at least one bevelled surface, said distal tip forming the most distal portion of said bevelled surface.

3. The apparatus of claim 2, wherein said bevelled surface terminates at its widest point as a heel located between said distal tip and said transverse conduit.

4. The apparatus of claim 1, wherein said elongate body is hollow, forming a working diameter in said device and wherein the distal tip is solid.

5. The apparatus of claim 4 wherein the apparatus additionally comprises an outer sleeve extending along the exterior surface of said elongate body.

6. The apparatus of claim 5, wherein the sleeve is expandable and said sleeve, when expanded, increases the working diameter of said apparatus.

7. The apparatus of claim 5, wherein said sleeve forms a cannula which can be peeled away.

8. The apparatus of claim 1, wherein said elongate body is substantially cylindrical.

9. The apparatus of claim 1, wherein the cross-sectional diameter is between 4.0 mm–10.0 mm.

10. The apparatus of claim 1, wherein said acute angle is at least 25°.

11. The apparatus of claim 1, wherein said body comprises surgical grade steel.

12. The apparatus of claim 1, wherein said body comprises a heat-stable polymer.

13. The apparatus of claim 1 wherein said elongate body has an anterior face and a posterior face, and wherein said conduit traverses said apparatus from said posterior face to said anterior face.

14. The apparatus of claim 13 wherein said bevelled surface extends along said posterior face from the distal tip to a position beneath said transverse conduit.

15. The apparatus of claim 14, wherein the body of said apparatus comprises an elongated hollow sleeve exiting at said conduit, wherein the hollow sleeve extends from said proximal end of the apparatus to said conduit, said hollow sleeve serving as a guide for the introduction and removal of one or more surgical tools through the proximal end of said apparatus through said transverse conduit.

16. The apparatus of claim 15, wherein said tip comprises the end of a guide needle extending through said elongate hollow body.

17. The apparatus of claim 16, wherein said guide needle is removable from said elongate hollow body.

18. A surgical apparatus for accessing the spinal foramen comprising:

an elongate body extending substantially along a first axis with a cross-sectional diameter of at least 3.0 mm, said body having a proximal end and a distal end, wherein said elongate body is hollow, forming a working diameter in said device and a conduit having a cross-sectional diameter of at least 2.0 mm positioned along the distal one-eighth of said body, said conduit extending substantially along a second axis and traversing said apparatus, said second axis positioned at an acute angle relative to said first axis.

19. The apparatus of claim 18, wherein said distal end comprises a tip that is sufficiently sharp to puncture disc tissue thereby anchoring said apparatus in said tissue.

20. The apparatus of claim 19, wherein said distal end further comprises at least one bevelled surface, said distal tip forming the most distal portion of said bevelled surface.

21. The apparatus of claim 20, wherein said bevelled surface terminates at its widest point as a heel located between said distal tip and said transverse conduit.

22. The apparatus of claim 18, wherein said elongate body is substantially cylindrical.

23. The apparatus of claim 18, wherein the cross-sectional diameter is between 4.0 mm–10.0 mm.

24. The apparatus of claim 18, wherein said acute angle is at least 25°.

25. The apparatus of claim 18, wherein said body comprises surgical grade steel.

26. The apparatus of claim 18, wherein said body comprises a heat-stable polymer.

27. The apparatus of claim 18 wherein the apparatus additionally comprises an outer sleeve extending along the exterior surface of said elongate body.

28. The apparatus of claim 27, wherein the sleeve is expandable and said sleeve, when expanded, increases the working diameter of said apparatus.

29. The apparatus of claim 28, wherein said distal end comprises a guide needle extending through said elongate hollow body, said guide needle having a tip that is sufficiently sharp to puncture disc tissue.

30. The apparatus of claim 29, wherein said guide needle is removable from said elongate hollow body.

31. The apparatus of claim 27, wherein said sleeve forms a cannula which can be peeled away.

32. The apparatus of claim 18, wherein said distal end comprises a guide needle extending through said elongate hollow body, said guide needle having a tip that is sufficiently sharp to puncture disc tissue.

33. The apparatus of claim 32, wherein said guide needle is removable from said elongate hollow body.

* * * * *